United States Patent
Kobayashi et al.

(10) Patent No.: US 10,322,185 B2
(45) Date of Patent: Jun. 18, 2019

(54) CONTROLLED RELEASE CARRIER FOR DRUGS CONTAINING SILK FIBROIN POROUS MATERIAL

(71) Applicants: Hitachi Chemical Company, Ltd., Tokyo (JP); St. Marianna University, School of Medicine, Kanagawa (JP); National Institute of Agrobiological Sciences, Ibaraki (JP)

(72) Inventors: Kazutoshi Kobayashi, Ibaraki (JP); Kunihiro Suto, Ibaraki (JP); Naosuke Sumi, Ibaraki (JP); Hajime Inoue, Kanagawa (JP); Yasushi Tamada, Ibaraki (JP)

(73) Assignees: HITACHI CHEMICAL COMPANY, LTD., Tokyo (JP); ST. MARIANNA UNIVERSITY, SCHOOL OF MEDICINE, Kanagawa (JP); NATIONAL INSTITUTE OF AGROBIOLOGICAL SCIENCES, Ibaraki (JP)

( * ) Notice: Subject to any disclaimer, the term of this patent is extended or adjusted under 35 U.S.C. 154(b) by 0 days.

(21) Appl. No.: 14/396,495

(22) PCT Filed: Apr. 24, 2013

(86) PCT No.: PCT/JP2013/062106
§ 371 (c)(1),
(2) Date: Oct. 23, 2014

(87) PCT Pub. No.: WO2013/161896
PCT Pub. Date: Oct. 31, 2013

(65) Prior Publication Data
US 2015/0094262 A1    Apr. 2, 2015

(30) Foreign Application Priority Data

Apr. 25, 2012   (JP) .................................. 2012-100024

(51) Int. Cl.
    *A61K 47/42*    (2017.01)
    *A61K 38/18*    (2006.01)
    *A61K 9/00*    (2006.01)
    *A61K 47/36*    (2006.01)
    *A61K 35/62*    (2006.01)

(52) U.S. Cl.
CPC ............ *A61K 47/42* (2013.01); *A61K 9/0014* (2013.01); *A61K 35/62* (2013.01); *A61K 38/1808* (2013.01); *A61K 38/1825* (2013.01); *A61K 38/1858* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 8,192,760 B2 * | 6/2012 | Hossainy | A61K 9/0024 424/484 |
| 8,742,069 B2 * | 6/2014 | Kaplan | A61L 27/227 530/300 |
| 9,090,703 B2 * | 7/2015 | Kobayashi | A61K 8/64 |
| 9,440,005 B2 * | 9/2016 | Tamada | A61L 27/227 |
| 2012/0039813 A1 | 2/2012 | Tansil et al. | |

FOREIGN PATENT DOCUMENTS

| | | |
|---|---|---|
| CN | 101905035 A | 12/2010 |
| JP | 1-118544 A | 5/1989 |
| JP | 1-254621 A | 10/1989 |
| JP | 5-43453 A | 2/1993 |
| JP | 8-175981 A | 7/1996 |
| JP | 9-192211 A | 7/1997 |
| JP | 3412014 B2 | 3/2003 |
| JP | 2004-123576 A | 4/2004 |
| JP | 2007-520614 A | 7/2007 |
| JP | 2008-502739 A | 1/2008 |
| WO | 2005123114 A2 | 12/2005 |
| WO | 2008/118133 A2 | 10/2008 |
| WO | 2009-113522 A1 | 9/2009 |
| WO | 2010/116994 A1 | 10/2010 |
| WO | 2010/141133 A2 | 12/2010 |
| WO | 2011/126031 A1 | 10/2011 |

OTHER PUBLICATIONS

Meinel et al. Bone 37: 688-698, 2005.*
Vepari et al. Prog. Polym. Sci. 32: 991-1007, 2007.*
Tamada Biomacromolecules 6: 3100-3106, 2005.*
Pritchard et al. Expert Opin. Drug Deliv. 8(6): 797-811, 2001.*
Supplementary European Search Report dated Sep. 4, 2015, for European Application No. 13781683.1.

* cited by examiner

*Primary Examiner* — Suzanne M Noakes
(74) *Attorney, Agent, or Firm* — Fitch, Even, Tabin & Flannery, LLP

(57) ABSTRACT

The present invention can provide a controlled drug release carrier formed by using a silk fibroin porous material, which has high drug controlled release rate, controllability of the drug controlled release speed, high strength, easy handleability, skin care properties from high biocompatibility, high water retentivity, and capability of efficiently retaining a drug.

6 Claims, 15 Drawing Sheets

CONTROLLED RELEASE CARRIER FOR DRUGS CONTAINING SILK FIBROIN POROUS MATERIAL

BACKGROUND

Technical Field

The present invention relates to a controlled drug release carrier.

Background Art

Conventionally, oral administration is known as a method of administering a drug to a patient. However, oral administration has disadvantages. One potential disadvantage is digestive trouble caused as a side effect of the drug. Another potential disadvantage is first pass metabolism of the drug by the liver cannot be prevented, because the liver cannot be bypassed. The difficulty controlling administration of a drug within a narrow therapeutic window of the drug is yet another disadvantage of oral administration.

As a means of addressing these disadvantages, drug formulations permitting percutaneous administration have been tried. Percutaneous administration formulations control penetration of the drug through the skin by using an active substance having a biological activity of facilitating percutaneous absorption of the drug stably for a long period of time. As the active substance, a surfactant or penetrant may be used. However, many of such active substances may actually damage dermal tissue and produce undesired side effects.

In addition, a covering material in which a drug is mixed in a base material, such as an oil solution, in the same way as a poultice to control release speed have been attempted. However, covering materials have a problem of low water retentivity and low water adsorption to dampen the affected area of the body. This produces an effect on the skin and makes it hard to apply the covering material to a wound with exudate.

As another method of controlling release properties of a drug, a method of controlling the transdermal penetration of the drug by retaining the medicinal properties in drug carries such as a gel or a porous material of synthetic polymers or natural polymers have been attempted (Patent Documents 1 and 2).

Moreover, a controlled release carrier having controlled release properties by resolving the carrier itself is proposed (Patent Documents 3 to 5). On the other hand, silk has a high biocompatibility among natural polymers, and thus conventionally used for sutures, which is known to have high safety. Silk is formed or sericin and fibroin protein. A variety of methods are proposed for processing silk. For example, hydrogels formed of silk fibroin have been attempted (Patent Document 6).

Patent Document 1: JP-A-8-175981
Patent Document 2: JP-T-2007-520614
Patent Document 3: JP-A-5-43453
Patent Document 4: JP-A-9-192211
Patent Document 5: JP-A-2004-123576
Patent Document 6: Japanese Patent No. 3412014

SUMMARY OF THE INVENTION

Figure 1:
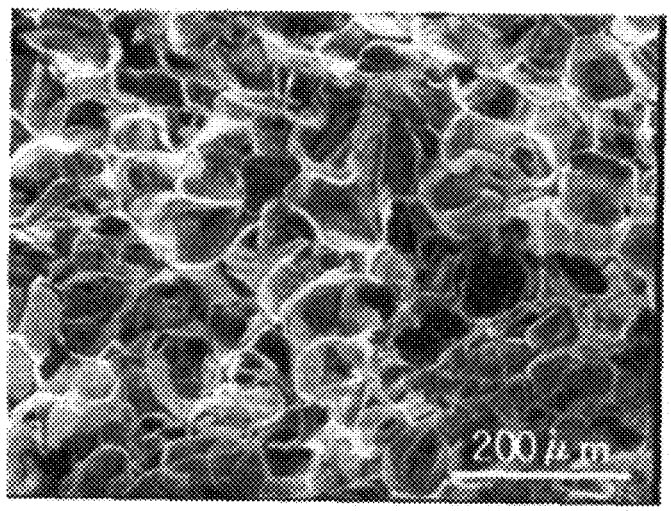
FIG. 1 shows a scanning electron microscopic photograph of a cross section of the porous material prepared in Example 1.
Figure 2:
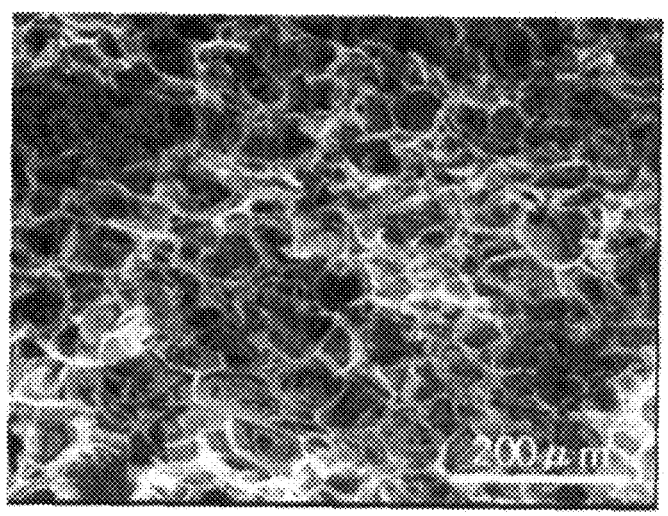
FIG. 2 shows a scanning electron microscopic photograph of a cross section of the porous material prepared in Example 2.
Figure 3:
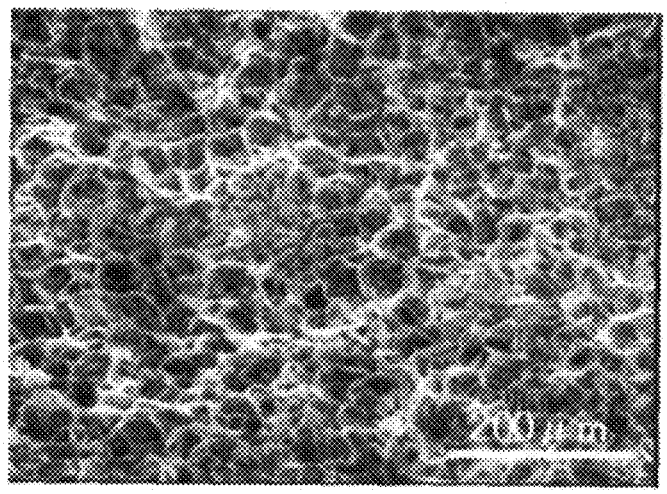
FIG. 3 shows a scanning electron microscopic photograph of the cross section of a porous material prepared in Example 3.
Figure 4:
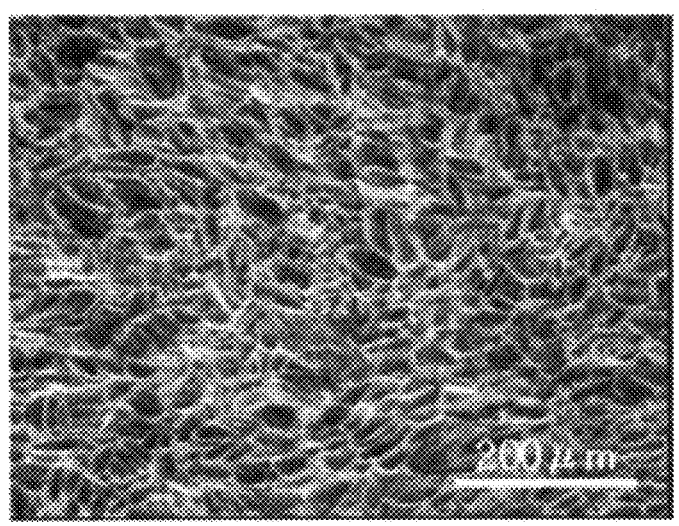
FIG. 4 shows a scanning electron microscopic photograph of a cross section of the porous material prepared in Example 4.
Figure 5:
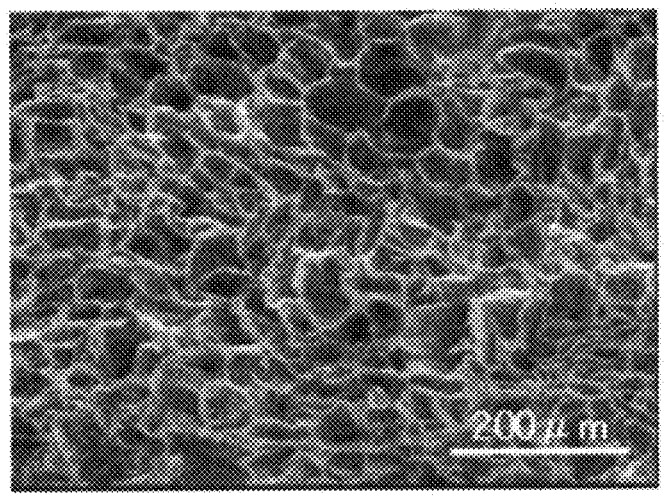
FIG. 5 shows a scanning electron microscopic photograph of a cross section of the porous material prepared in Example 5.
Figure 6:
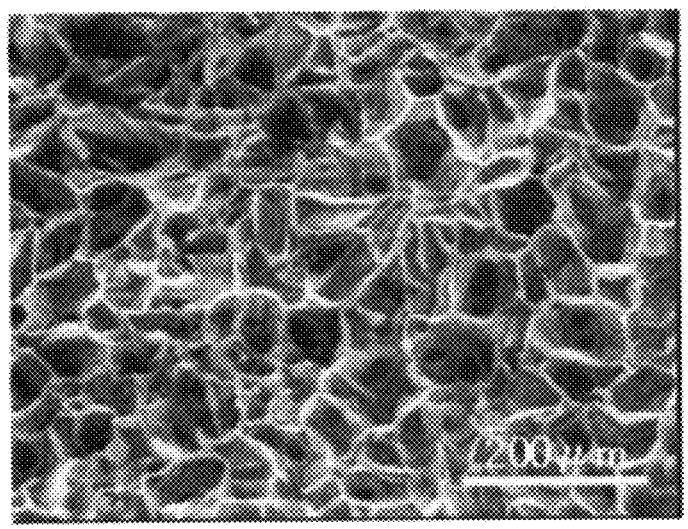
FIG. 6 shows a scanning electron microscopic photograph of a cross section of the porous material prepared in Example 6.
Figure 7:
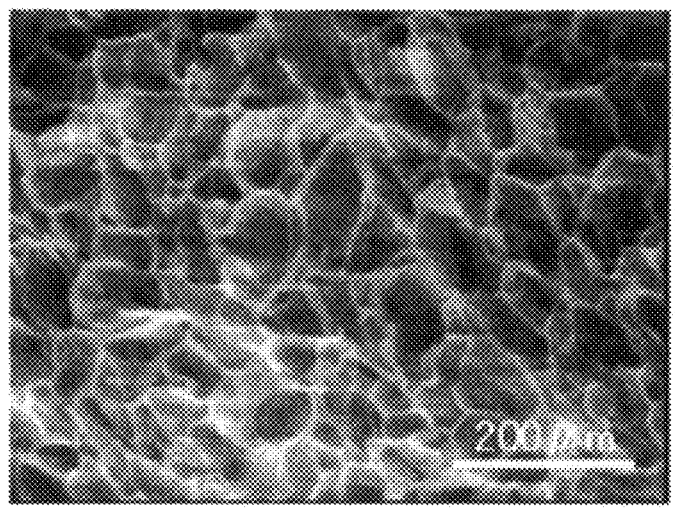
FIG. 7 shows a scanning electron microscopic photograph of a cross section of the porous material prepared in Example 7.
Figure 8:
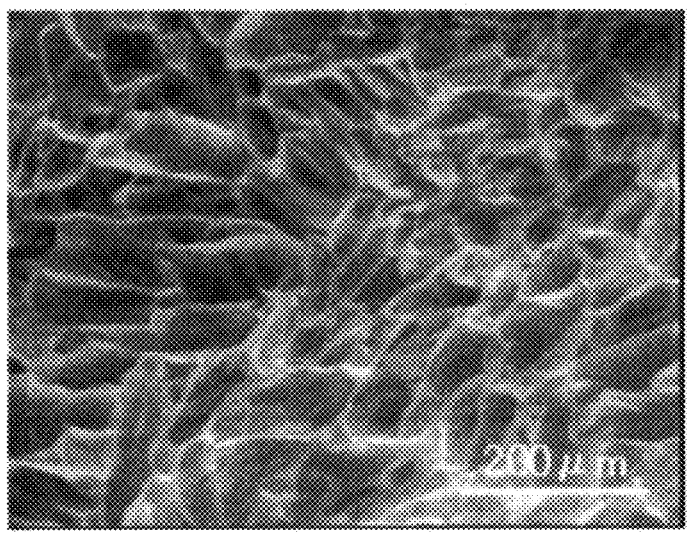
FIG. 8 shows a scanning electron microscopic photograph of a cross section of the porous material prepared in Example 8.
Figure 9:
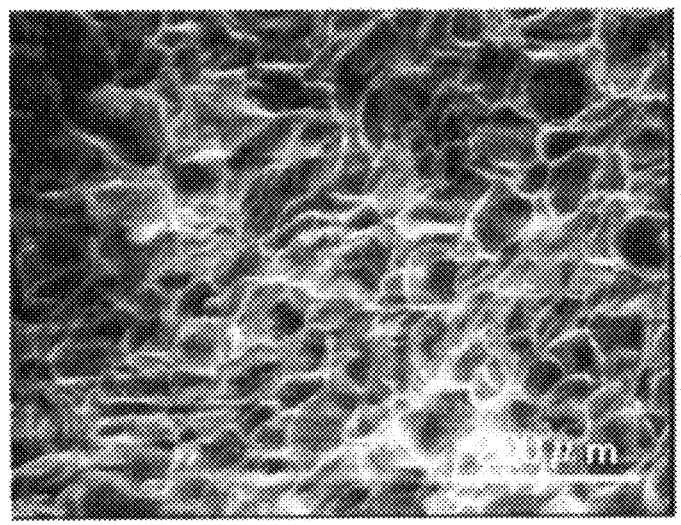
FIG. 9 shows a scanning electron microscopic photograph of a cross section of the porous material prepared in Example 9.
Figure 10:
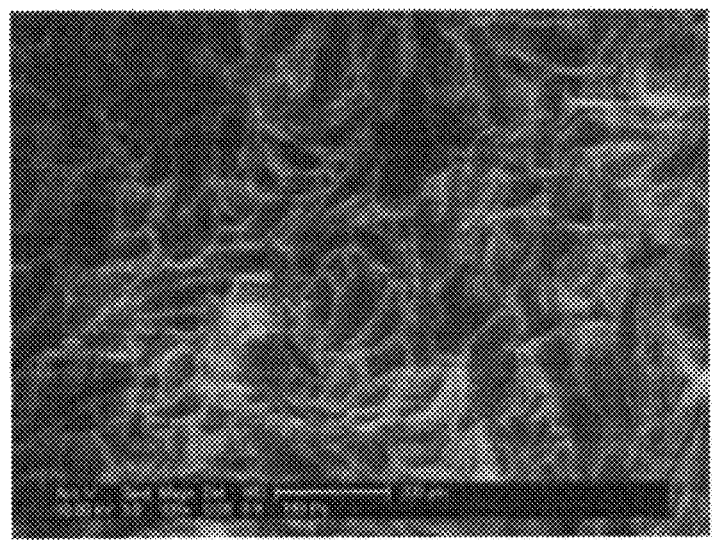
FIG. 10 shows a scanning electron microscopic photograph of a cross section of the porous material prepared in Example 10.
Figure 11:
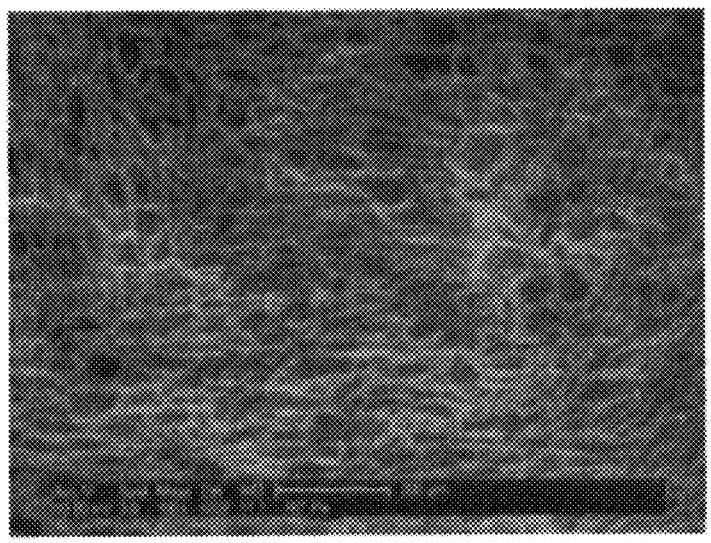
FIG. 11 shows a scanning electron microscopic photograph of a cross section of the porous material prepared in Example 11.
Figure 12:
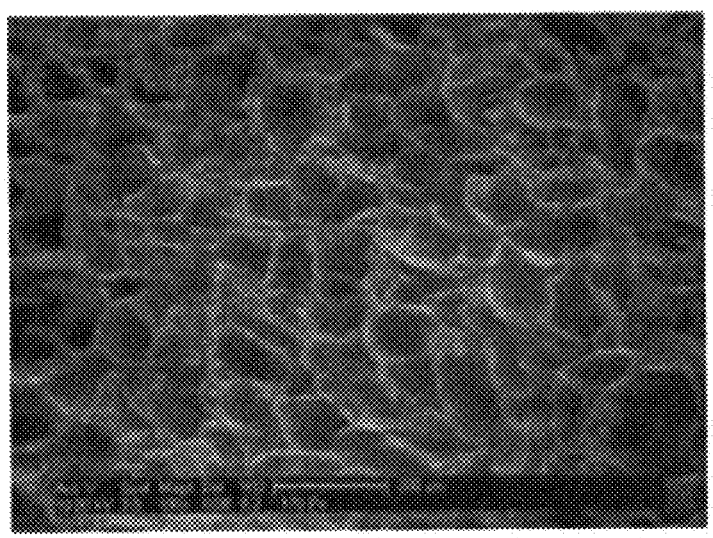
FIG. 12 shows a scanning electron microscopic photograph of a cross section of the porous material prepared in Example 12.
Figure 13:
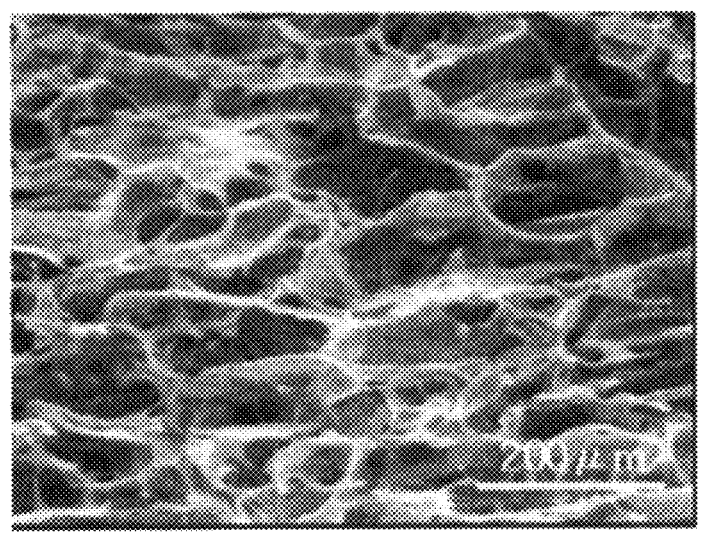
FIG. 13 shows a scanning electron microscopic photograph of a cross section of the porous material prepared in Example 13.
Figure 14:
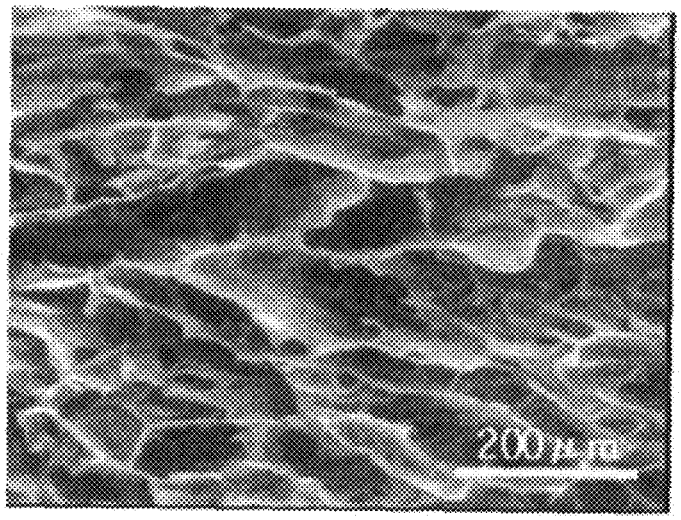
FIG. 14 shows a scanning electron microscopic photograph of a cross section of the porous material prepared in Example 14.
Figure 15:
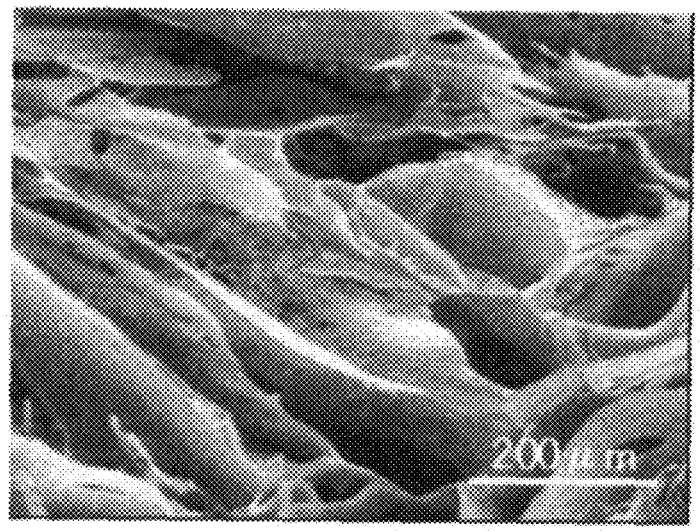
FIG. 15 shows a scanning electron microscopic photograph of a cross section of the porous material prepared in Example 15.
Figure 16:
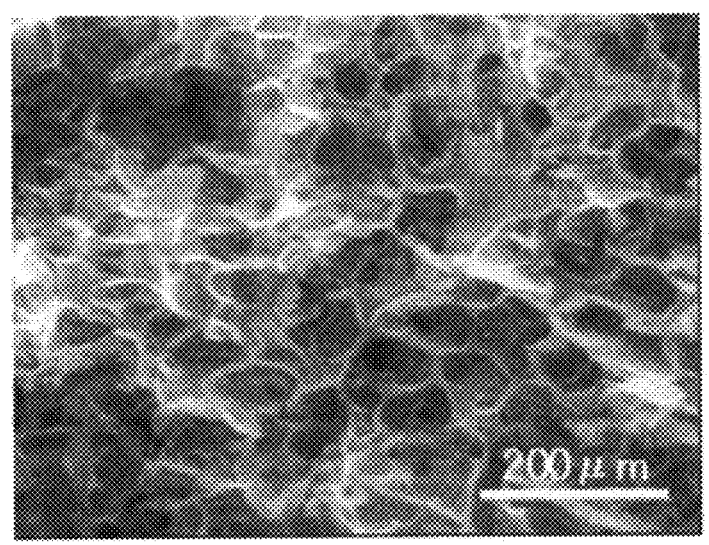
FIG. 16 shows a scanning electron microscopic photograph of a cross section of the porous material prepared in Example 16.
Figure 17:
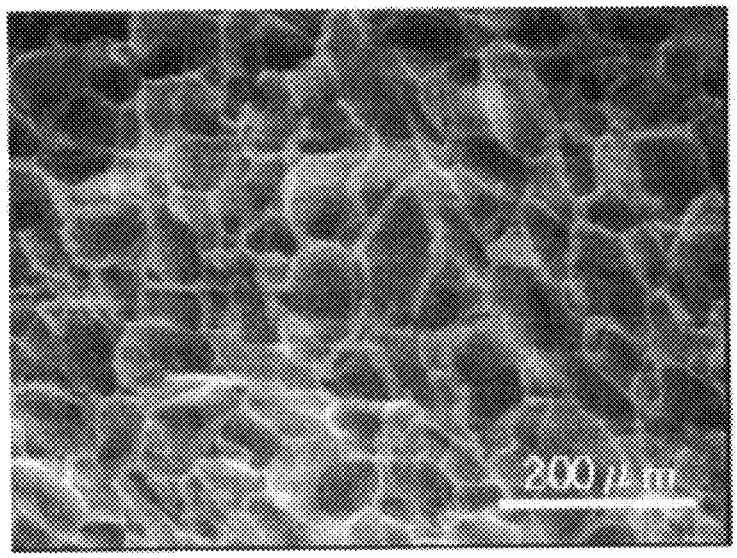
FIG. 17 shows a scanning electron microscopic photograph of a cross section of the porous material prepared in Example 17.
Figure 18:
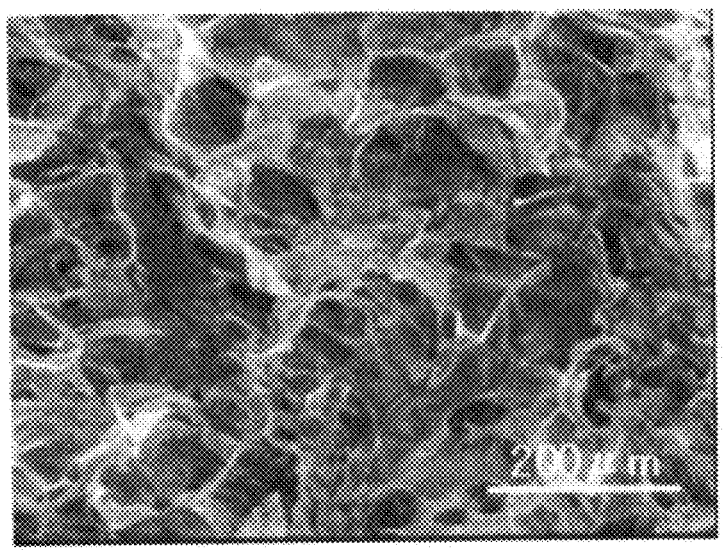
FIG. 18 shows a scanning electron microscopic photograph of a cross section of the porous material prepared in Example 18.
Figure 19:
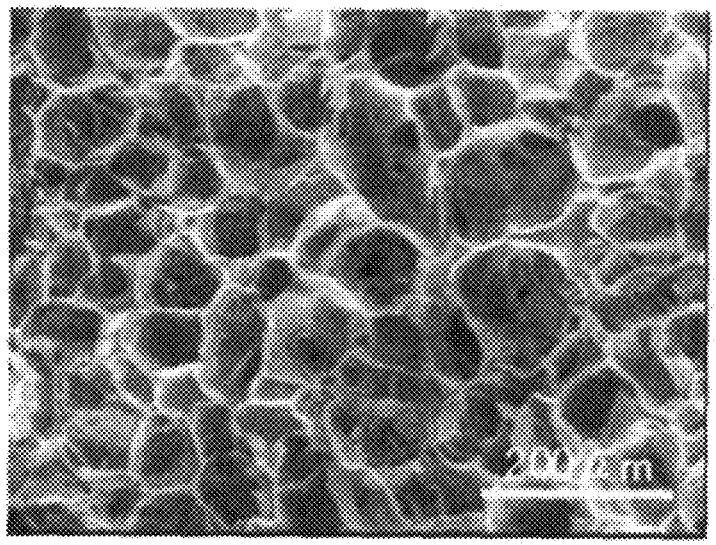
FIG. 19 shows a scanning electron microscopic photograph of a cross section of the porous material prepared in Example 19.
Figure 20:
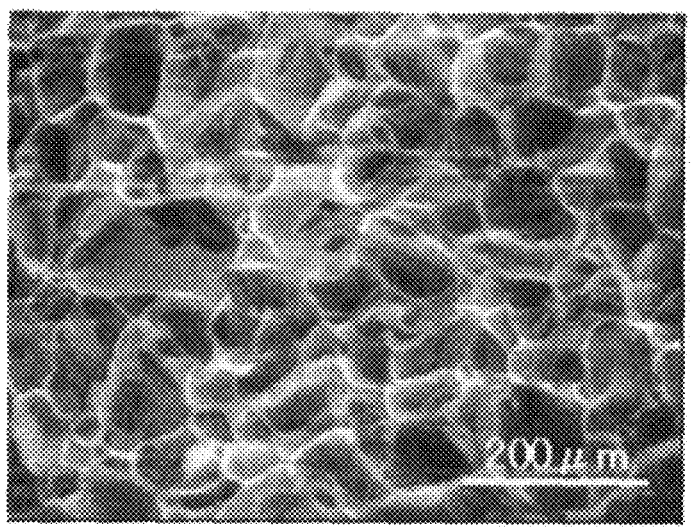
FIG. 20 shows a scanning electron microscopic photograph of a cross section of the porous material prepared in Example 20.
Figure 21:
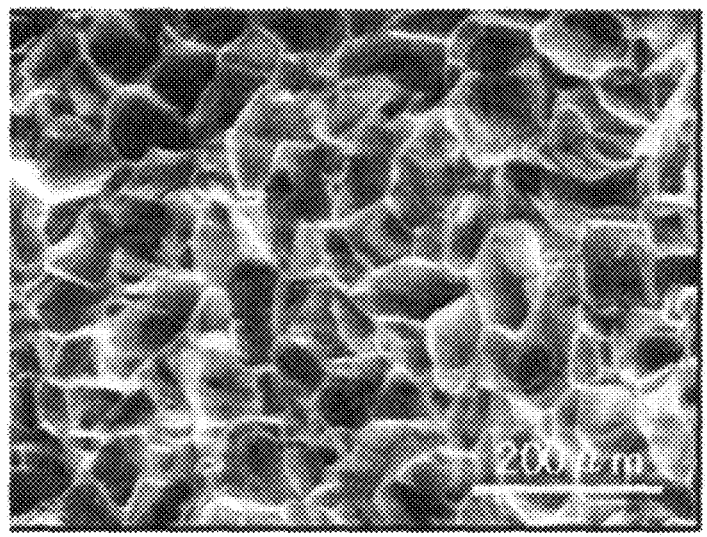
FIG. 21 shows a scanning electron microscopic photograph of a cross section of the porous material prepared in Example 21.
Figure 22:
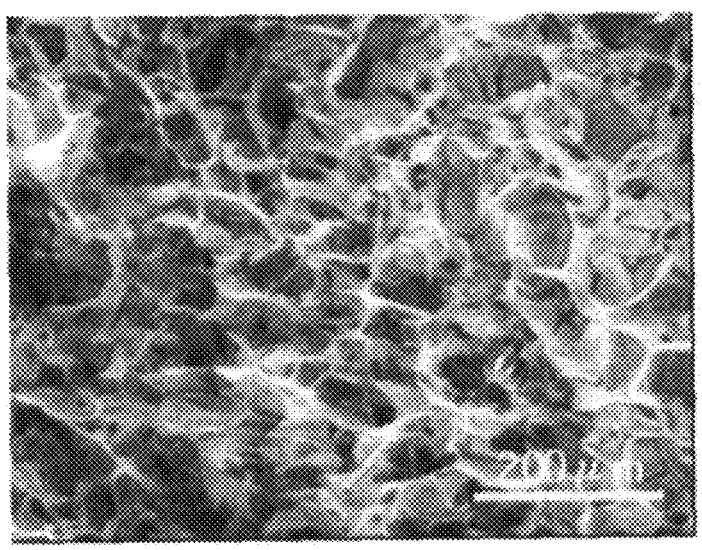
FIG. 22 shows a scanning electron microscopic photograph of a cross section of the porous material prepared in Example 22.
Figure 23:
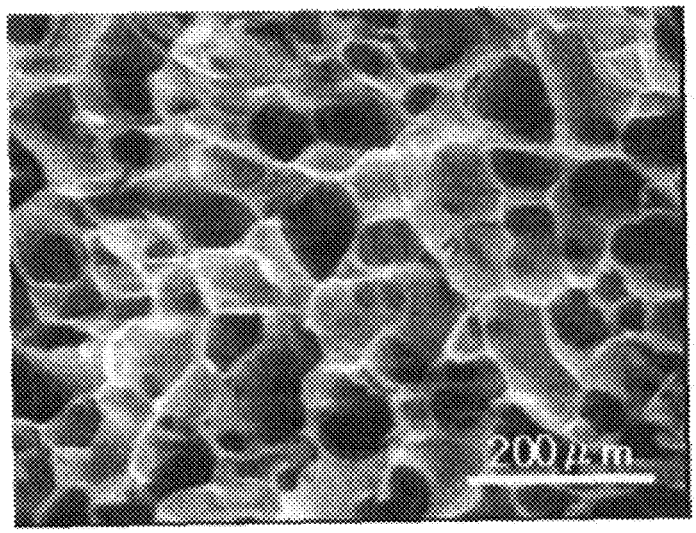
FIG. 23 shows a scanning electron microscopic photograph of a cross section of the porous material prepared in Example 23.

Problems to be Solved by the Invention

When used as drug carriers, the synthetic polymers described in Patent Documents 1 and 2 have low affinity to the skin, low water retentivity, difficult controlling release speed, and low controlled release efficiency. Natural polymers used as drug carriers have an advantage of high affinity to the skin, but have the disadvantage of low strength. Thus, the strength of natural polymers is required to be increased by using a crosslinked body formed of a cross-linker, using a strengthening agent, or wrapping the natural polymers themselves in gauze or the like. However, if a cross-linker is used to increase strength, the remaining crosslinking agent may negatively affect the skin. If a strengthening agent is used, the structure of the drug carrier may be complicated, or a part of the drug carrier may remain on the skin when peeled off. When natural polymers are wrapped in gauze or the like to increase strength, the skin is contacted with the conventional covering material, such as gauze, but not gel or porous material with high biocompatibility and high water retentivity. Thus, if wrapped in a conventional covering material, natural polymers have an insufficient effect.

The controlled drug release carriers as described in Patent Documents 3 to 5 are hardly resolved outside the body and thus are difficult to apply to the skin or the like. Moreover, when applied as controlled drug release carriers, hydrogels as described in Patent Document 6 have difficulty controlling the rate of drug release.

The objective of the present invention is to provide a controlled drug release carrier with a high drug release rate, controllability of the drug release speed, high strength, that is easy handled, that provides skin care properties from high biocompatibility, that has high water retentivity, and that is capable of efficiently retaining a drug.

Means for Solving the Problem

As a result of their extensive studies, the inventors found that the folling invention can solve the above-identified problems. A summary of the present invention is described below.

1. A controlled drug release carrier formed by using a silk fibroin porous material.

2. The controlled drug release carrier according to 1, in which the silk fibroin porous material is treated by a water-soluble high polymer.

3. The controlled drug release carrier according to 2, in which the water-soluble high polymer is material containing at least one kind selected from a polysaccharide and a polyamino acid.

4. The controlled drug release carrier according to 3, in which the polysaccharide contains at least one kind selected from heparin and chondroitin sulfate.

5. The controlled drug release carrier according to any one of 1 to 4, in which the drug to be carried contains a growth factor.

6. The controlled drug release carrier according to 5, in which the growth factor is at least one kind selected from a fibroblast growth factor (FGF), a platelet derived growth factor (PDGF), and an epidermal growth factor (EGF).

7. The controlled drug release carrier according to any one of 1 to 6, in which the tensile strength of the porous material is 0.1 to 400 kPa.

Effect of the Invention

The present invention can provide a controlled drug release carrier with a high drug release rate, controllability of the drug release speed, high strength, that is easy handled, that provides skin care properties from high biocompatibility, that has high water retentivity, and that is capable of efficiently retaining a drug.

DETAILED DESCRIPTION OF PREFERRED EMBODIMENTS

Controlled Drug Release Carrier

The controlled drug release carrier of the present invention is characterized by a silk fibroin porous material.

The silk fibroin porous material is herein referred to as a porous material containing silk fibroin and preferably having an average pore size of 1 to 300 μm.

The silk fibroin porous material comprising the controlled drug release carrier of the present invention has excellent controlled release properties and thus can be used as is without being treated. However, the silk fibroin porous material is preferably used after a surface treatment in order to control release speed. The method of surface treatment is not limited in particular, but includes physical treatments with gamma rays, electron rays, and plasma.

The method of surface treatment also includes: oxidant treatments with ozone, hydrochloric acid, and the like; alkaline treatments with a sodium hydroxide aqueous solution and the like; chemical modification treatments with reagents having a reactive group such as an aldehyde group or an epoxy group; and treatments with a water-soluble high polymer and a low molecular weight material. Among these, it is desired for the silk fibroin porous material to be treated under a mild condition, preferably with a water-soluble high polymer, in order to maintain the behavior of the silk fibroin porous material.

The water-soluble high polymer is preferably a material with high biological safety, particularly a polysaccharide or a polyamino acid. Examples of preferable polysaccharides include starch, cellulose, chitin, chitosan, agarose, carrageenan, heparin, chondroitin sulfate, hyaluronic acid, and pectin. Carboxymethylcellulose and the like formed by chemically modifying these polysaccharides can also be used.

Examples of preferable polyamino acid include polylysine, polyalginic acid, polyaspartic acid, and polyglutamic acid. In the present invention, these polysaccharide and polyamino acid can be used alone or in combination with two or more kinds.

In the present invention, the use of the silk fibroin porous material after surface treatment or the like can easily maintain control over the drug release rate while providing a high drug release rate. Moreover, a high concentration of polysaccharide or the polyamino acid as the water-soluble high polymer provides a controlled drug release carrier having a higher controlled release speed.

These polysaccharides or polyamino acids are preferably used after being dissolved in, for example, water, buffer solution, or saline. In this case, the concentration is preferably 0.05 to 50 U/mL, more preferably 0.1 to 45 U/mL, further more preferably 0.2 to 35 U/mL. A concentration falling within this range efficiently increases the controlled release speed. The controlled release speed can be easily controlled by adjusting the concentration.

The tensile strength of the silk fibroin porous material is preferably 0.1 to 400 kPa. A tensile strength of 0.1 kPa or more provides sufficient strength to permit easily handling of the controlled drug release carrier and reduces the controlled drug release carrier remaining on the skin. On the other hand, a tensile strength of 400 kPa or less maintains adhesion to the skin. From these viewpoints, the tensile strength is more preferably 1 to 300 kPa, more preferably 5 to 200 kPa.

The controlled drug release carrier of the present invention preferably has a high water retention rate to retain absorbed water. The high water retention rate enables absorbed exudate to flow out. Specifically, the water retention rate calculated by the following method is preferably 85 to 100%. A water retention rate of 85% or more retains and prevents exudate from flowing out. From these viewpoints, the water retention rate of the silk fibroin porous material is more preferably 87 to 100%, most preferably 90 to 100%.

Method of Calculating Water Retention Rate

The water retention rate is a value obtained by the following calculation. The porous material is formed into 60×30×20 mm measurement sample. After being sufficiently immersed in pure water, the sample is weighed (Wc). This sample is immersed in pure water again. Then, a glass plate (MSA coated micro-glass slide available from Matsunami Glass Inc., Ltd., 7 6×52 mm), the surface of which is wet with pure water, is placed at a tilt of 45 degrees. On the glass plate, the sample is placed with the largest face (60×30 mm) down and with the length direction up and down, and left still for 10 minutes. Subsequently, the sample is weighed (Wd). The value calculated by the following expression using the weights (Wc) and (Wd) of the sample is defined as the water retention rate.

Water retention rate (%)=100−(Wc−Wd)×100/(Wc)

The water absorption rate of the porous material is preferably 0.1 to 1000 μL/s, more preferably 1 to 100 μL/s, most preferably 20 to 30 μL/s. A water absorption rate of 0.1 μL/s or more enables the controlled drug release carrier to promptly absorb exudate, so that less exudate flows out of the controlled drug release carrier. A water absorption rate of 1000 μL/s or less prevents the controlled drug release carrier from excessively absorbing exudate as to maintain a wet condition in the contacted area.

The evaporation rate is preferably 0.01 to 0.2 g/m2/s, more preferably 0.03 to 0.15 g/m2/s, most preferably 0.06 to 0.1 g/m2/s. An evaporation rate of 0.01 g/m2/s or more enables the controlled drug release carrier to continuously absorb exudate. On the other hand, an evaporation rate of 0.2 g/m2/s or less can efficiently maintain the controlled drug release carrier of the present invention under wet conditions. The water absorption rate and the evaporation rate are values obtained in the following manner. As long as the water absorption rate and the evaporation rate of the porous layer fall within the respective ranges, the present invention produces an excellent effect.

Method of Calculating Water Absorption Rate

100 μL of pure water is dropped onto the silk fibroin porous material, and the time taken to absorb the pure water is measured. The water absorption rate is a value calculated by the following expression using the measured time. The measurement was made 5 times, and the water absorption rate is averaged over these measurements.

Water absorption rate(μL/s)=Amount of dropped pure water/Time taken to absorb water The form of the controlled drug release carrier of the present invention is not limited and thus may be appropriately selected as desired. The form is preferably a sheet from the viewpoint of the usability. The size of the sheet can be optionally set. The thickness of the sheet can be optionally set according to the dosage of drug.

The drug that can be contained in the controlled drug release carrier of the present invention is not limited in particular. Examples of the drug preferably include endogenous proteins promoting specific cells to be reproduced and differentiated in the body, specifically growth factors such as an epidermal growth factor (EGF), an insulin-like growth factor (IGF), a transforming growth factor (TGF), a nerve growth factor (NGF), a vascular endothelial growth factor (VEGF), a platelet derived growth factor (PDGF), and fibroblast growth factors (FGF) such as a basic fibroblast growth factor (b-FGF) and an acidic fibroblast growth factor (a-FGF), and a hepatocyte growth factor (HGF); antihistamines such as diphenhydrazine hydrochloride, chlorpheniramine, and diphenylimidazole; corticosteroids such as hydrocortisone, prednisolone, paramethasone, beclomethasone propionate, flumethasone, betamethasone, beclometasone propionate, dexamethasone, triamcinolone, triamcinolone acetonide, fluocinolone, fluocinolone acetonide, fluocinolone acetonide acetate, and clobetasol propionate; antiphlogistic analgetics such as acetaminophen, mefenamic acid, flufenamic acid, indomethacin, diclofenac, alclofenac, oxyphenbutazone, phenylbutazone, ibuprofen, flurbiprofen, salicylic acid, methyl salicylate, L-menthol, and camphor; antibiotics such as penicillin, oxytetracycline, fradiomycin sulfate, erythromycin, chloramphenicol, cefalexin, and tetracycline; vitamin preparations such as vitamin A, ergocalciferol, cholecalciferol, octotiamine, and riboflavin butyrate; and anesthetics such as benzocaine, lidocaine, and ethyl aminobenzoate. These drugs can be used alone or in combination with two or more kinds.

In addition to these drugs, an auxiliary absorbent, for example, isopropyl myristate, isopropyl palmitate, N-methyl pyrrolidone, N-ethyl pyrrolidone, N,N-diethyl-m-triamide, N,N-di ethyl acetamide, hyaluronic acid, salicylic acid, crotamiton, diethyl sebacate, lauryl alcohol, dimethyl sulphoxide, or desmethyl sulfoxide can be blended as appropriate. By blending these auxiliary absorbents, the capability to promote absorption of the drug by the barrier membrane of the skin and the capability to promote penetration of the drug into the blood can be provided.

The amount of the above-mentioned drugs is appropriately determined according to the drug to be selected. As a measure of dosage, the drug is added so that about 1 μg to 300 mg/12 cm$^2$ of drug (thickness: 2 mm) is carried on the controlled drug release carrier.

The drug can be retained by being impregnated within or spread onto the silk fibroin porous material. These drugs can be used alone or in combination with two or more kinds.

A solvent can be used when the above-mentioned drugs are blended. The solvent to be used is not limited in particular as long as it is not harmful to humans, preferably the solvent is chemically-inactive with respect to the drug to be used, and capable of dissolving or dispersing the drug to be used. Specifically, water and polyalcohol can be used alone, or as a mixed solvent in which two or more kinds of polyalcohols are combined. Water is the most preferable solvent from the viewpoint of safety to humans. Examples of the polyalcohol solvents preferably include glycerin, propylene glycol, and sorbit.

A water-soluble polymer can be added in order to improve the dissolubility of the drug in the solvent. Examples of the water-soluble polymer preferably include gelatin, sodium alginate, tragacanth rubber, starch, methyl cellulose, ethyl cellulose, hydroxyethyl cellulose, carboxymethyl cellulose, polyvinyl pyrrolidone, polyvinyl alcohol, and sodium polyacrylate.

The controlled drug release carrier of the present invention is formed in a sheet shape as mentioned above. Possible configurations include a silk fibroin porous material sheet preferably fixed with a dressing film, a bandage, an adhesive tape, or the like. The use of a dressing film or the like can prevent body fluid from being exposed and flowing out to provide an environment suitable for moist healing when the silk fibroin porous material is pressured or brought into contact with the skin. Moreover, the controlled drug release carrier can be used in the digestive tract and in the body.

The controlled drug release carrier, that is, the silk fibroin porous material is preferably maintained under a wet condition in order to controllably release drug. When a wound with exudate is subjected to moist healing, the released drug can penetrate into the affected part through the exudate. When no exudate is present, the silk fibroin porous material can be used after being wetted with saline or the like.

Method of Producing Silk Fibroin Porous Material

The method of producing the silk fibroin porous material will be explained below. The silk fibroin porous material used in the present invention can be produced by, for example, adding a specific additive to a silk fibroin aqueous solution, and freezing and then thawing this aqueous solution.

The silk fibroin to be used here only has to be produced by silkworms such as domesticated silkworms, wild silkworms, and Japanese oak silkworms. The production method is not limited in particular. Silk fibroin has poor solubility and thus is hardly dissolved in water. To obtain the silk fibroin aqueous solution, any known techniques may be adopted. However, a technique in which silk fibroin is dissolved in a high-concentration lithium bromide aqueous solution, and the solution is then subjected to desalting by means of dialysis and concentration by means of air-drying is simple and easy, and thus preferable.

In the method of producing the silk fibroin porous material, the concentration of the silk fibroin is preferably 0.1 to 40% by mass, more preferably 0.5 to 20% by mass, further more preferably 1.0 to 12% by mass in the silk fibroin aqueous solution with an additive or the like as described later. By allowing the concentration of fibroin to fall within the foregoing range, it is possible to efficiently produce a porous material with sufficient strength.

Possible additives preferably include organic solvent, aliphatic carboxylic acid, and amino acid. The additive is not limited in particular but preferably is water soluble, more preferably highly water soluble. The acid dissociation constant of an aliphatic carboxylic acid used to produce the silk fibroin porous material is preferably 5.0 pKa or less, more preferably 3.0 to 5.0 pKa, further more preferably 3.5 to 5.0 pKa.

Possible organic solvents preferably include methanol, ethanol, isopropanol, butanol, t-butanol, glycerol, dimethyl sulphoxide (DMSO), dimethyl formamide (DMF), pyridine, acetonitrile, and acetone. These organic solvents can be used alone or in combination with two or more kinds.

As the aliphatic carboxylic acid, for example, a saturated or unsaturated monocarboxylic acid, dicarboxylic acid, and tricarboxylic acid with 1 to 6 carbon atoms can be preferably used. More specific examples of the aliphatic carboxylic acid preferably include formic acid, acetic acid, propionic acid, butyric acid, succinic acid, lactic acid, acrylic acid, 2-butene acid, and 3-butene acid. These aliphatic carboxylic acids can be used alone or in combination with two or more kinds.

Possible amino acid preferably include monoaminocarboxylic acids such as valine, leucine, isoleucine, glycine, alanine, serine, threonine, and methionine; aliphatic amino acids such as monoaminodicarboxylic acids (acidic amino acids) such as aspartic acid and glutamic acid; aromatic amino acids including phenylalanine; and amino acids having a heterocycle including hydroxyproline. Among these, from the viewpoint of easily adjusting the shape, acidic amino acids and oxyamino acids such as hydroxyproline, serine and threonine are preferable. From the same viewpoint, among the acidic amino acids, monoaminocarboxylic acid is more preferable, and aspartic acid or glutamic acid is particularly preferable; and among the oxyamino acids, hydroxyproline is more preferable. These amino acids can be used alone or in combination with two or more kinds.

Incidentally, the amino acid includes L-type and D-type optical isomers. Since the use of L-type and the D-type does not produce an observable difference in structure and mechanical characteristics, any of these amino acids may be used.

The content of the additive in the silk fibroin aqueous solution is preferably 0.1 to 18% by mass, more preferably 0.1 to 5.0% by mass, most preferably 0.2 to 4.0% by mass based on the total amount of the silk fibroin aqueous solution. By allowing the additive content to fall within the foregoing range, it is possible to produce a silk fibroin porous material with sufficient strength. An additive content of 18.0% or less by mass hardly allows the aqueous solution to gelate while the silk fibroin aqueous solution in which the additive is added is left still. Thus, a silk fibroin porous material is stably obtained with high quality.

The silk fibroin aqueous solution containing the additive is cast into a mold or a container and frozen in a low-temperature thermostat, followed by a thawing process to produce a silk fibroin porous material. The freezing temperature is not limited as long as the silk fibroin aqueous solution containing the additive freezes. However, the freezing temperature is preferably about −10 to −30° C. The freezing time is preferably 4 or more hours at a predetermined freezing temperature so that the silk fibroin aqueous solution is sufficiently frozen and maintained in its frozen state for a certain time.

As for a freezing method, the silk fibroin aqueous solution may be frozen by decreasing its temperature to a freezing temperature at once. However, from the standpoint of obtaining a silk fibroin porous material having high mechanical strength, it is preferable that the silk fibroin aqueous solution be held at about −5° C. for 2 or more hours and then have its temperature decreased to the freezing temperature. By adjusting the time taken to decrease the temperature from −5° C. to the freezing temperature, the structure and the strength of the silk fibroin porous material can be controlled to some extent.

The frozen silk fibroin aqueous solution is thawed to obtain a silk fibroin porous material. The method of thawing the silk fibroin aqueous solution is not limited in particular. Possible thawing methods preferably include naturally thawing the silk fibroin aqueous solution and storing the silk fibroin aqueous solution in a thermostat.

The obtained silk fibroin porous material contains the above-mentioned additive. If required according to the intended application, the additive only has to be removed from the silk fibroin porous material by an appropriate method. Immersing the silk fibroin porous material in pure water is the simplest and easiest method of removing the additive. Alternatively, the additive can be removed together with water by freeze-drying the silk fibroin porous material.

By appropriately selecting the mold or the container, the silk fibroin porous material can be formed into a shape corresponding to the mold, such as a sheet shape, a block shape, a tubular shape, or a spherical shape. In the present invention, the silk fibroin porous material is preferably formed into a sheet shape as mentioned above.

The mold and the container are not limited in particular as long as their shape and their form do not allow the silk fibroin aqueous solution to flow out. The material of the mold and the container is preferably a material with high thermal conductivity, such as iron, stainless steel, aluminum, gold, silver, or copper so as to obtain a silk fibroin porous material with a uniform structure. Moreover, the wall thickness of the mold and the container is preferably 0.5 mm or more from the viewpoint of the function and the prevention of the deformation due to swelling and the like during the freezing, and more preferably 1 to 3 mm from the viewpoint of the easy handling and cooling efficiency.

The mold and the container used can be provided with a sheet layer on the inner wall in contact with the silk fibroin aqueous solution. This enables a film layer to be placed on the surface of the silk fibroin porous material. In other words, a silk fibroin porous material having a porous layer and a film layer can be obtained. The porous layer has a sponge-like porous structure in which a large number of pores exist, while the film layer does not substantially have pores.

According to the characteristics of the sheet layer provided on the inner wall of the mold or the container, the structure and the thickness of the film layer can be controlled.

Possible sheets used for the sheet layer preferably include sheets formed of fluorine resins such as polytetrafluoroethylene (PTFE), tetrafluoroethylene-hexafluoropropylene copolymers (FEP), and tetrafluoroethylene-perfluoroalkyl vinyl ether copolymers (PFA); and mold release-treated sheets formed of polyethylene terephthalate (PET) and polypropylene (PP). When these sheets are used, a smooth film layer with a few pores can be obtained. When a film layer is undesired, a sheet with a rough surface such as filter paper can be used. Sheets only have to be appropriately selected according to the intended application of the silk fibroin porous material. A sheet with a thickness of 1 mm or less, which hardly blocks thermal conduction, is preferred.

The silk fibroin porous material is obtained through a cutting process after the thawing process. If the porous material consists only of the porous layer in a suitable sheet shape as the controlled drug release carrier for extracorporeal application, a porous surface can be obtained by cutting away the film layer, as an alternative to altering the sheet material of the container. As a result, a sheet formed of the porous material consisting of only the porous layer can be obtained. Specifically, for example, a sheet formed using a block-shaped mold or container with a Teflon sheet on the inner wall may have its four sides removed and the porous layer cut off to obtain such a sheet formed of the porous layer. Furthermore, a mold or a container with a Teflon sheet on only one side of the inner wall and with filter paper on the other sides can provide a porous material having the film layer on only one side.

A silk fibroin porous material having the above-mentioned film layer decreases the liquid permeability by decreasing the rates of liquid drug moving, evaporating, and diffusing through the pores. Thus, when used a silk fibroin porous material having a film layer preferably has the porous layer in contact with the skin and the film layer on the side opposite the skin. Such a controlled drug release carrier for extracorporeal application efficiently retains liquid drugs and suppresses vaporization and diffusion of the drugs.

The number of pores in the film layer can be controlled. Thus, the film layer can have a small number of pores as appropriate. Since the film layer has a very few pores, the surface is smooth compared with that of the porous layer. Thus, by using this film layer as the skin side to control the liquid permeability, the release speed of drugs can be controlled.

The production method of the controlled drug release carrier of the present invention provides silk fibroin porous materials having various structures, such as a structure consisting of only a porous layer and a structure consisting of a porous layer and a film layer with various properties, so that the controlled drug release carrier can be easily used for various purposes.

EXAMPLES

The present invention is hereunder more specifically described by reference to the following Examples, but it should be construed that the present invention is not limited to these Examples.

Example 1

Preparation of Silk Fibroin Aqueous Solution

Fibroin powder (trade name: fibroin IM, available from KB Seiren, Ltd.) was added to a 9 M lithium bromide aqueous solution. After the solution was centrifugalized, precipitated insoluble matter was removed, dialysis relative to ultra-pure water was performed repeatedly to obtain a silk fibroin aqueous solution. Subsequently, the resulting silk fibroin aqueous solution was concentrated in a dialysis tube by means of air-drying. A formic acid aqueous solution was added to the concentrated liquid as an additive to obtain a silk fibroin solution having a silk fibroin concentration of 5% by mass and a formic acid concentration of 2% by mass.

Production of Silk Fibroin Porous Material

This silk fibroin aqueous solution was cast into a mold made of an aluminum plate (inner size: 80 mm×40 mm×4 mm), which was then placed in a low-temperature thermostat (NCB-3300, manufactured by EYELA) and freeze-stored.

Freezing Condition

The low-temperature thermostat was previously cooled to −5° C. The mold having the silk fibroin aqueous solution was placed in the low-temperature thermostat, held for 2 hours, cooled to −20° C., and then held at this temperature for 5 hours. The frozen sample was left to warm to room temperature by means of natural thawing, taken out from the mold, and then immersed in ultra-pure water. The ultra-pure water was exchanged twice a day for 3 days to remove the formic acid used.

Method of Measuring Mechanical Characteristics

The mechanical characteristics of the obtained silk fibroin porous material were evaluated using a micro tester 5548 Model available from INSTRON. The maximum rupture strength (tensile elastic modulus) and the maximum strain (elongation) were measured using a 40 mm×4 mm×4 mm test piece cut from the prepared silk fibroin porous material and pulling the test piece at 2 mm/min. Then, the tensile elastic modulus was determined from the gradient of a graph between the strength and the strain. The obtained results are shown in Table 1. The measurement results show an average value obtained from five test pieces from a prepared porous material, further cutting out five test pieces from a porous material prepared on a different day, and measuring the ten test pieces.

The structure of the obtained silk fibroin porous material was observed using a scanning electron microscope, XL30-FEG, manufactured by Philips, and the measurement was carried out in a low-vacuum non-vapor deposition mode at an accelerating voltage of 10 kV. Incidentally, as for the structure of the silk fibroin porous material, the interior of the porous material which had been exposed by cutting, but not the surface of the porous material, was observed. The scanning electron microscopic photograph of the cross section of the obtained porous material is shown in FIG. 1.

Examples 2 to 23

Silk fibroin porous materials were obtained in the same manner as Example 1, except that the additives shown in Table 1 were used in place of formic acid. In Examples 10 to 12, the concentration of the additive was set to 1% by mass (see Table 2). The evaluation result of the mechanical characteristics, the water retention rates, and the water absorption rates of the obtained silk fibroin porous materials are shown in Table 1 and Table 2. Scanning electron microscopic photographs of cross sections of the obtained porous materials are each shown in FIGS. 2 to 23. The water retention rates and the water absorption rates were measured as described above.

Comparative Example 1

A commercially available polyurethane sponge (available from Sumitomo 3 M Limited) was cut to provide a measurement sample (60 mm×30 mm×20 mm). Then, the water retention rate of the sample was measured. The obtained result is shown in Table 1.

TABLE 1

|  | Additive | Tensile strength [kPa] | Maximum strain | Tensile elastic modulus [kPa] | Water retention rate [%] |
|---|---|---|---|---|---|
| Example 1 | Formic acid | 80.0 | 0.64 | 203.6 | 98.1 |
| Example 2 | Acetic acid | 118.9 | 0.76 | 290.4 | 98.7 |
| Example 3 | Propionic acid | 98.0 | 0.70 | 229.3 | 97.9 |
| Example 4 | Butyric acid | 145.7 | 0.53 | 287.3 | 98.3 |
| Example 5 | Succinic acid | 101.6 | 0.54 | 158.8 | 98.3 |
| Example 6 | Lactic acid | 116.8 | 0.59 | 189.6 | 98.8 |
| Example 7 | Acrylic acid | 154.9 | 0.70 | 322.2 | 97.5 |
| Example 8 | 2-butene acid | 96.3 | 0.45 | 261.7 | 97.3 |
| Example 9 | 3-butene acid | 107.0 | 0.49 | 272.9 | 98.2 |
| Example 10 | Hydroxyproline | 83.2 | 0.62 | 162.2 | 98.4 |
| Example 11 | Glutamic acid | 120.4 | 0.68 | 288.9 | 98.4 |
| Example 12 | Aspartic acid | 113.7 | 0.65 | 252.3 | 97.9 |
| Example 13 | Methanol | 28.0 | 0.54 | 42.7 | 97.2 |
| Example 14 | Ethanol | 29.1 | 0.21 | 175.6 | 97.9 |
| Example 15 | Isopropanol | 14.3 | 0.36 | 26.8 | 98.2 |
| Example 16 | Butanol | 57.3 | 0.39 | 141.9 | 97.8 |
| Example 17 | t-butanol | 39.1 | 0.30 | 93.3 | 97.5 |
| Example 18 | Glycerol | 5.5 | 0.13 | 44.1 | 98.9 |
| Example 19 | DMSO | 42.6 | 0.53 | 86.4 | 97.4 |
| Example 20 | DMF | 66.2 | 0.64 | 192.6 | 97.2 |
| Example 21 | Pyridine | 71.6 | 0.53 | 251.4 | 98.2 |
| Example 22 | Acetonitrile | 72.4 | 0.53 | 180.2 | 98.0 |
| Example 23 | Acetone | 72.6 | 0.52 | 234.1 | 98.1 |
| Comparative Example 1 | Polyurethane | — | — | — | 69.0 |

TABLE 2

|  | Additive | | Water absorption rate (μL/s) |
|---|---|---|---|
|  | Type | Concentration (% by mass) |  |
| Example 1 | Formic acid | 2 | 28.55 |
| Example 2 | Acetic acid | 2 | 25 |
| Example 3 | Propionic acid | 2 | 25.5 |
| Example 4 | Butyric acid | 2 | 20.1 |
| Example 5 | Succinic acid | 2 | 23.98 |
| Example 6 | Lactic acid | 2 | 27.1 |
| Example 7 | Acrylic acid | 2 | 21.8 |
| Example 8 | 2-butene acid | 2 | 23.9 |
| Example 9 | 3-butene acid | 2 | 23.0 |
| Example 10 | Hydroxyproline | 1 | 26.9 |
| Example 11 | Glutamic acid | 1 | 26.2 |
| Example 12 | Aspartic acid | 1 | 26.2 |
| Example 13 | Methanol | 2 | 32.4 |
| Example 14 | Ethanol | 2 | 35.8 |
| Example 15 | Isopropanol | 2 | 38.9 |
| Example 16 | Butanol | 2 | 37.2 |
| Example 17 | t-butanol | 2 | 40.1 |
| Example 18 | Glycerol | 2 | 31.5 |
| Example 19 | DMSO | 2 | 29.7 |
| Example 20 | DMF | 2 | 33.9 |
| Example 21 | Pyridine | 2 | 34.2 |
| Example 22 | Acetonitrile | 2 | 34.8 |
| Example 23 | Acetone | 2 | 32.1 |
| Comparative Example 1 | Polyurethane | — | 256.4 |

FIG. 1 clarifies that the porous layer composing the silk fibroin porous material obtained in Example 1 has a relatively thin wall and few ten micro meter of pores. FIGS. 2 to 23 clarify that the silk fibroin porous materials obtained in examples 2 to 23 have the same structure as the porous material obtained in Example 1.

From the results shown in Table 1, the water retention rates of the silk fibroin porous materials obtained in Examples 1 to 23 fall within the range of 97 to 99%, which is higher than that of Comparative Example 1. The silk fibroin porous materials were confirmed to have the capacity to retain the absorbed exudate with hardly any of the absorbed exudate flowing out. From the results shown in Table 2, the water absorption rates of the silk fibroin porous materials obtained in Examples 1 to 23 fall within the range of 20 to 40 (µL/s), which is smaller than that of Comparative Example 1. The silk fibroin porous materials were confirmed to have the capacity to prevent the exudate from being excessively absorbed and to maintain a wet condition in the contacted area, while less exudate flowed out of the controlled drug release carrier.

Examples 24 to 26

As part of a nonclinical test on the safety of the silk fibroin porous material, a human patch test (skin sensitization patch test) was conducted. This human patch test (skin sensitization patch test) was to determine whether or not the silk fibroin porous materials irritate or induce allergic contact dermatitis in human skin.

The silk fibroin porous materials used in Examples 24 to 26 were prepared in the same manner as Example 1, except for utilizing a 264 mm×205 mm×1 mm mold made from an aluminum plate and using aspartic acid (same as Example 12), lactic acid (same as Example 6), and succinic acid (same as Example 5) as the additives in place of formic acid, respectively. To evaluate these silk fibroin porous material sheets, samples with a size of 10 mm×10 mm×1 mm were cut to prepare the respective patches of Examples 25 to 27.

The human patch test (skin sensitization patch test) was conducted on 50 healthy Japanese females aged 18 to 65 years. The above-mentioned patches were fixed to the subjects' back with a 20 mm×20 mm piece of hypoallergenic tape. The patches were fixed at least 15 mm apart from each other. For comparison, a 10 mm×10 mm non-woven cotton cloth was fixed with a 20 mm×20 mm piece of hypoallergenic tape. The fixed patches were removed 48 hours after application, and then the subjects' skin reaction was observed. The patches were reapplied to their respective places, and then the subjects' skin reaction was observed 48 hours later. The application and the observation were repeated 9 times in total. Then 2 weeks later, the application and the observation were repeated every 48 hours 4 times.

As a result, 2 subjects had very mild erythema once in Examples 24 and 25 during the test, but the erythema disappeared by the end of the test. This proves that the silk fibroin porous material sheets are very hypoallergenic and cause no allergic sensitization.

Furthermore, 1 subject had very mild erythema once in Example 26 during the test, but the erythema disappeared by the end of the test. This proves that the silk fibroin porous material sheet is very hypoallergenic and causes no allergic sensitization.

Example 27

Except for using a made from an aluminum sheet having an interior of 130 mm×80 mm×12 mm, a silk fibroin porous material was prepared in the same manner as Example 6.

As part of a nonclinical test on the safety of the silk fibroin porous material, a primary skin irritation test and a skin sensitization test were conducted. These tests were conducted based on "Standards for the Reliability of Application" (Article 43, Enforcement Regulations, Pharmaceutical Affairs Law) according to "Basic Principles of Biological Safety Evaluation Required for Application for Approval for Manufacture (Import) of Medical Devices" (Pharmaceutical Affairs Bureau Notification No. 0213001 dated Feb. 13, 2003) and "Reference Material on Basic Principles of Testing Methods to Evaluate Biological Safety of Medical Devices" (Notice from the Office Medical Devices Evaluation No. 36 dated Mar. 19, 2003).

Primary Skin Irritation Test

Silk fibroin porous material (consisting of only the porous layer) obtained as described above was cut into 5 mm×5 mm×5 mm test pieces.

Silk fibroin porous material extracted with isotonic sodium chloride solution and with sesame oil liquid, respectively, were applied to rabbits to examine the presence or absence of local irritation (tissue damage and inflammation induction). Specifically, isotonic sodium chloride solution or sesame oil was added to the test pieces and heated at 120° C. in an autoclave for 1 hour to prepare the test solutions. Aside from this, only the extraction solvent (isotonic sodium chloride solution or sesame oil) was processed on the same condition to prepare control samples. 6 male rabbits were used per test solution. The test solutions and the control samples were each administered in 0.5 mL to the intact skin and the abraded skin on the back of each rabbit.

The test solution extracted with isotonic sodium chloride solution developed very mild or negligible erythema in 3 of the 6 rabbits one hour after administration. These 3 rabbits also had erythema caused by an isotonic sodium chloride solution control sample. This erythema was comparable in degree to that caused by the test solution. The test solution produced a primary irritation index of 0.3 and thus was classified as "a negligible irritant."

The test solution extracted with sesame oil developed very mild erythema in 4 of the 6 rabbits one hour after administration. These 4 rabbits also had erythema caused by a sesame oil control sample. This erythema was comparable in degree to that caused by the test solution. The test solution produced a primary irritation index of 0.1 and thus was classified as "a negligible irritant."

Skin Sensitization Test

The methanolic extract of the silk fibroin porous material prepared in Example 27 was applied to 10 male guinea pigs to examine the presence or absence of sensitization of the guinea pigs' skin by maximization test method.

Before the skin sensitization test, the extraction ratio was calculated using acetone and methanol in order to determine the appropriate extraction solvent. As a result, methanol has a higher extraction ratio than acetone and was thus was determined as the extraction solvent to be used for the skin sensitization test.

10 mL of methanol was added to a test piece cut from the silk fibroin porous material prepared in Example 27 and then subjected to extraction at room temperature with a constant temperature shaking incubator. Extraction was conducted for 24 or more hours. As control groups, a negative control group sensitized to olive oil and a positive control group sensitized to 1-chloro-2,4-dinitrobenzene were prepared.

The number of the animals of each control group was 5. Then, responses to 6.25, 12.5, 25, 50, and 100% by mass of extract liquids and acetone were elicited in the test solution-administered group and the negative control group. As a result, this group had no observed skin reaction during the observation periods of 24, 48, and 72 hours after the elicitations.

On the other hand, a response to 0.1% by mass of 1-chloro-2,4-dinitrobenzene was elicited in the positive control group. As a result, all the 5 animals clearly had a positive reaction 24, 48, and 72 hours after the elicitation.

From this test result, the silk fibroin porous material prepared in Example 27 was determined to contain no materials causing skin sensitization.

Since the silk fibroin porous material prepared in Example 27 was classified as "a negligible irritant" and contained "no materials causing skin sensitization," this silk fibroin porous material is confirmed to have high safety and excellent usability as a controlled drug release carrier of the present invention.

Example 28

Figure 24:
FIG. 24 shows a diagram illustrating the silk fibroin porous material left still in the culture dish in which fibroblasts was plane-cultured in Example 28.

To confirm no harmful effects of the silk fibroin porous material on cells, the silk fibroin porous material prepared in Example 2 was left still in a culture dish of fibroblasts previously plane-cultured. If the silk fibroin porous material itself or a component eluted therefrom is cytotoxic, fibroblasts centered around the silk fibroin porous material should be detached, or the whole cultured cells should be lost. However, as shown in FIG. 24, the surface itself of the silk fibroin porous material is non-cytotoxic and that cells migrated and approached evenly around the silk fibroin porous material, without creation of an inhibition circle. The upper part (deep color part) of FIG. 24 is the silk fibroin porous material side.

After non-toxicity was confirmed, fibroblasts were disseminated to the surface of the silk fibroin porous material and then cultured for 2 weeks according to a conventional method. The fibroblasts disseminated to the surface of the silk fibroin porous material was confirmed to be migrated to the dish after a certain period and cultured on the entire surface of the dish, and then the silk fibroin porous material was taken out to be subjected to histological stain.

Figure 25:
FIG. 25 shows a diagram illustrating fibroblasts cultured for 2 weeks after disseminated to the surface of the silk fibroin porous material in Example 28.

It was expected that the silk fibroin porous material with non-toxicity has excellent cell affinity as discussed above and that the cells would migrate, spread, and proliferate in and on the pores of the silk fibroin porous material. However, as shown in FIG. 25, adherence of the fibroblast and proliferation associated therewith were not seen on the surface of the silk fibroin porous material, and migration of and proliferation of fibroblast within the pores were not seen in the porous material. The deep color part of FIG. 25 shows fibroblasts.

Figure 26:
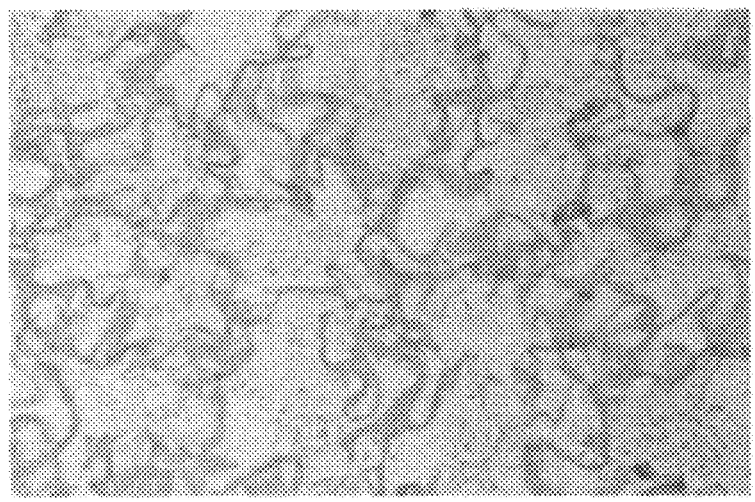
FIG. 26 shows a diagram illustrating fibroblasts cultured for 2 weeks after disseminated to the gelatin sponge in Example 28.

Then, a gelatin sponge (Spongel available from Astellas Pharma Inc.) as a hemostatic material obtained by being purified from swine collagen, which has the same porosity as the silk fibroin porous material has, was used in the same manner for the comparative experiment. As a result, the fibroblasts had an extremely high cell affinity, and migrated, spread, and proliferated in the pores, as shown in FIG. 26. In this case, it was found that a gelatin sponge can be used to arrest hemorrhage on the surface of a wound and to be filled in a defect but cannot avoid the adhesion to the wound site because of the cell adhesion.

On the other hand, since the silk fibroin porous material is non-cytotoxic and has low cell adhesion, despite high tissue affinity, the silk fibroin porous material does not interact with the surrounding tissue so as to prevent an interaction (adhesion) with the surrounding healthy tissue in the tissue repair of the lesion site. This proves that the silk fibroin porous material functions as an excellent anti-adhesive material. Anti-adhesive films called gelatin films are commercially available, but have high cell adhesion. Thus, gelatin films adhere to the surrounding tissue.

Figure 27:
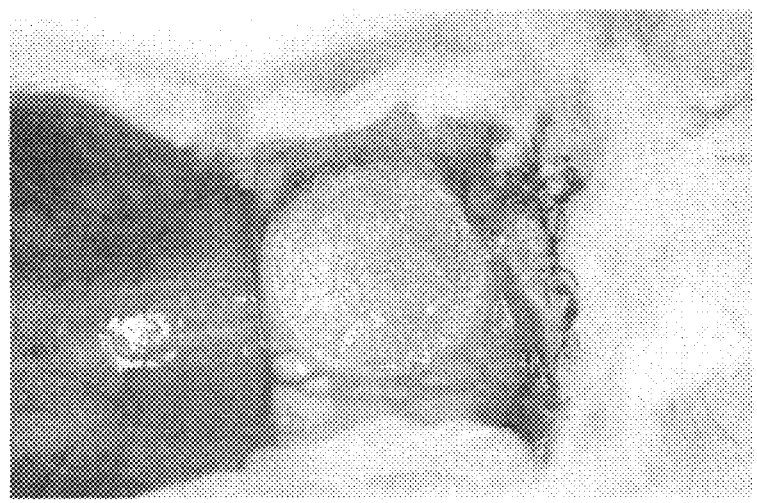
FIG. 27 is an image illustrating the results of the adhesive test of Example 28.

Based on these results, the silk fibroin porous material used in the present invention was formed into a silk sponge disk and then implanted under the skin of a mouse to examine foreign substance adhesion. As shown in FIG. 27, the silk fibroin porous material used in the present invention clearly bonded to one side of the implanted site but did not bond (adhere) to mucous membranes at the both sides. This proves that the silk fibroin porous material exhibits an excellent anti-adhesive effect.

Furthermore, the controlled drug release properties of a controlled drug release carrier formed by using a silk fibroin porous material was examined.

Example 29

A silk fibroin porous material (formed in a cylindrical sample with a diameter of 1 mm and a thickness of 2 mm) was obtained in the same manner as Example 1, except that the concentration of the silk fibroin porous material was 3% by mass and formic acid was replaced with acetic acid. The silk fibroin porous material was immersed in phosphate buffered saline (PBS) for about 1 hour and then air-dried at room temperature of 25° C. The silk fibroin porous material was impregnated and saturated with aqueous solution in which 500 ng of an epidermal growth factor (EGF) (available from Wako Pure Chemical Industries, Ltd.) in phosphate buffered saline (PBS). The sample of the silk fibroin porous material was prepared so as to contain 500 ng of the growth factor. The silk fibroin porous material impregnated with the growth factor is left still in a 12 well culture plate (available from Becton, Dickinson and Company). Then, 1 mL of Dulbecco's modified Eagle's (DME) medium (available from Gibco) was added to this silk fibroin porous material and left still in a moisture environment (condition: 37° C., 95% or more, 5% CO2). The medium was collected 24, 48, and 96 hours later and stored at −80° C. until the measurement.

The epidermal growth factor (EGF) was measured as described below.

Figure 28:
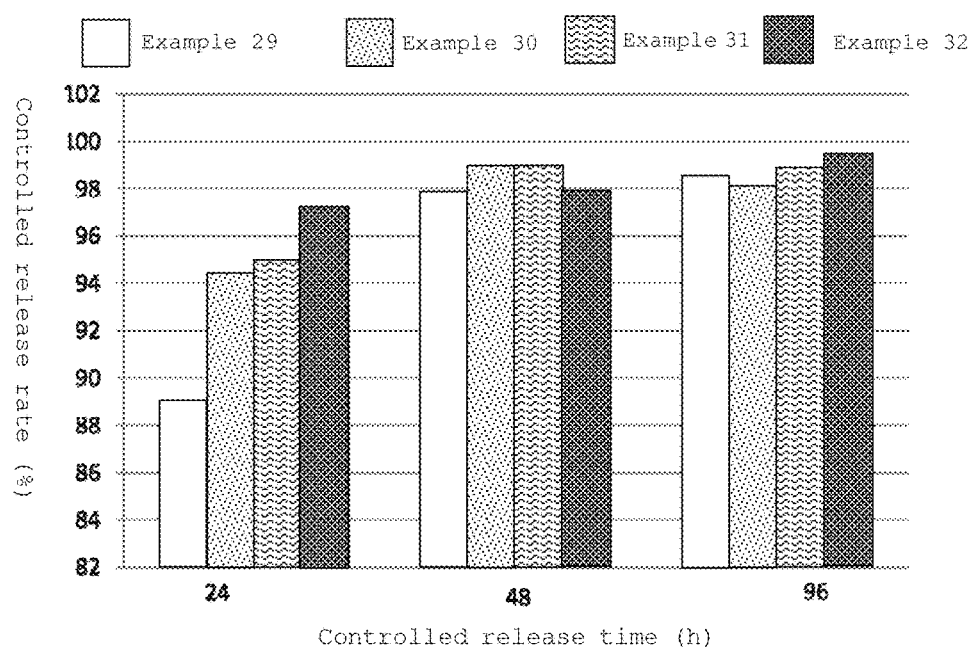
FIG. 28 shows a diagram illustrating the controlled release rates of Examples 29 to 32.

A human EGF EIA kit (Research and Development, Inc.) was used. Specifically, 0.1 mL of each obtained medium was added to a 96 well microplate which immobilizes anti-EGF antibodies and reacted at 37° C. for 2 hours. The wells were washed 5 times with phosphate buffered saline (PBS) containing surfactant, and then peroxidase-labelling anti-EGF secondary antibodies were added to the wells and then reacted at room temperature for 1 hour. Subsequently, the wells were washed 5 times in the same way, and then the color reagent was added to the wells and then reacted at room temperature for 20 minutes. Then, a reaction stopper was added, and the obtained colors were measured at 450 nm with a microplate reader. Subsequently, the controlled release amounts (W1) were calculated from a calibration curve prepared in the same manner. The controlled release rates of an epidermal growth factor (EGF), which were calculated from the following expression by using the obtained controlled release amounts (W1), are shown in FIG. 28.

$$(\text{Controlled release rate (\%) of EGF}) = (\text{Controlled release amount of EGF in culture medium}(W1)) / 500 \text{ ng} \times 100$$

Example 30

A silk fibroin porous material was obtained in the same manner as Example 29 except for previously immersing the silk fibroin porous material in phosphate buffered saline (PBS) aqueous solution containing 0.3 U/mL of heparin (available from MOCHIDA PHARMACEUTICAL CO., LTD.) for about 1 hour and then air-drying the silk fibroin porous material at room temperature of 25° C. The obtained silk fibroin porous material was evaluated in the same manner as Example 29. The obtained result is shown in FIG. 28.

Example 31

Except for setting the concentration of heparin to 3 U/mL, a silk fibroin porous material was prepared and evaluated in the same manner as Example 30. The obtained result is shown in FIG. 28.

Example 32

Except for setting the concentration of heparin to 30 U/mL, a silk fibroin porous material was prepared and evaluated in the same manner as Example 30. The obtained result is shown in FIG. 28.

As shown in FIG. 28, the results of Examples 29 to 32 clarify that the controlled release speed (controlled release time) of an epidermal growth factor (EGF) was dependent on the concentration of heparin when the silk fibroin porous material subjected to surface treatment with phosphate buffered saline (PBS) aqueous solution containing heparin. More specifically, as the concentration of heparin increases, the controlled release speed (controlled release time) tends to have peaked but increase. The controlled release rate was 98% or more.

Example 33

A silk fibroin porous material was obtained in the same manner as Example 29 except for previously immersing the silk fibroin porous material in phosphate buffered saline (PBS) containing 30 U/mL of heparin (available from MOCHIDA PHARMACEUTICAL CO., LTD.) for about 1 hour and then air-drying the silk fibroin porous material at room temperature of 25° C. The obtained silk fibroin porous material (formed in a cylindrical sample with a diameter of 1 mm and a thickness of 2 mm) was impregnated and saturated with aqueous solution in which 500 ng of a platelet derived growth factor (PDGF) (available from Sigma/Aldrich Japan) in phosphate buffered saline (PBS). The sample of the silk fibroin porous material was prepared so as to contain 500 ng of the growth factor. The silk fibroin porous material impregnated with the growth factor is left still in a 12 well culture plate (available from Becton, Dickinson and Company). Then, 1 mL of Dulbecco's modified Eagle's (DME) medium (available from Gibco) was added to this silk fibroin porous material and left still in a moisture environment (condition: 37° C., 95% or more, 5% CO2). The medium was collected 6, 12, 48, and 96 hours later and stored at −80° C. until the measurement.

The platelet derived growth factor (PDGF) was measured as described below.

Figure 29:
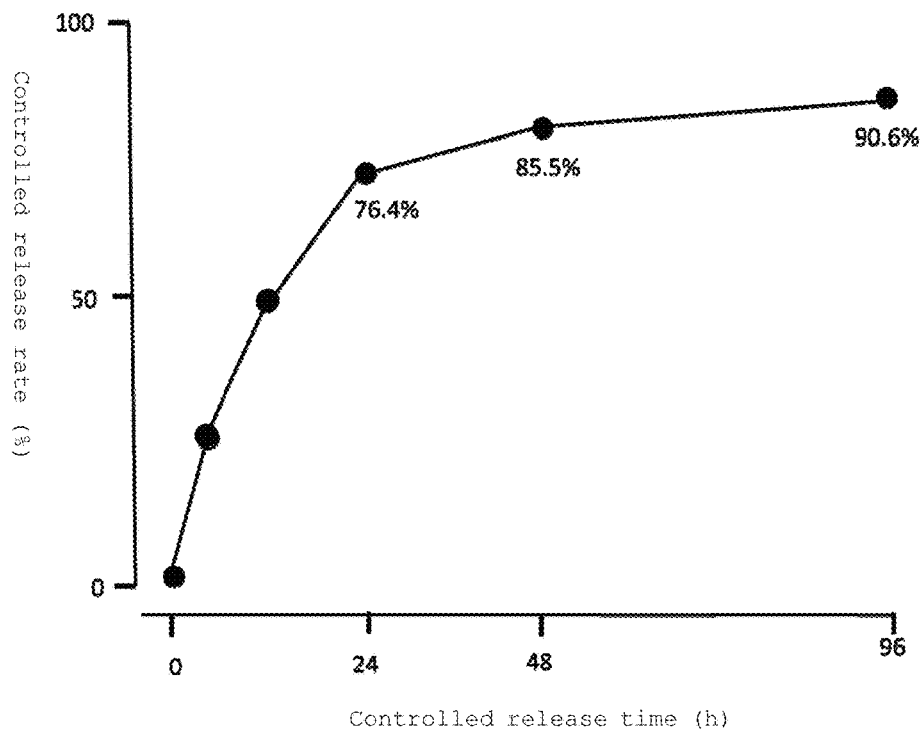
FIG. 29 shows a diagram illustrating the controlled release rate of a platelet derived growth factor (PDGF) to the culture medium in Example 33.

A human PDGF-BB EIA kit (Research and Development, Inc.) was used. Specifically, 0.1 mL of each obtained medium was added to a 96 well microplate which immobilizes anti-PDGF antibodies and then reacted at 37° C. for 2 hours. The wells were washed 5 times with phosphate buffered saline (PBS) containing surfactant, and then peroxidase-labelling anti-PDGF secondary antibodies were added to the wells and then reacted at room temperature for 1 hour. Subsequently, the wells were washed 5 times in the same way, and then the color reagent was added to the wells and then reacted at room temperature for 20 minutes. Then, a reaction stopper was added, and the obtained colors were measured at 450 nm with a microplate reader. Subsequently, the controlled release amount (W2) of PDGF was calculated from a calibration curve prepared in the same manner. The controlled release rates which were calculated from the following expression are shown in FIG. 29 as the controlled release rate of a platelet derived growth factor (PDGF) to a culture medium.

(Controlled release rate of PDGF (%))=(Controlled release amount of PDGF in culture medium ($W2$))/500 ng×100

The controlled release rate of a platelet derived growth factor (PDGF) was 90.6% for up to 96 hours. The platelet derived growth factor (PDGF) was confirmed to be released for 4 days.

Example 34

A silk fibroin porous material was obtained in the same manner as Example 29 except for previously immersing the silk fibroin porous material in phosphate buffered saline (PBS) containing 3 U/mL of heparin (available from MOCHIDA PHARMACEUTICAL CO., LTD.) for about 1 hour and then air-drying the silk fibroin porous material at room temperature of 25° C. The obtained silk fibroin porous material (formed in a cylindrical sample with a diameter of 1 mm and a thickness of 2 mm) was impregnated and saturated with aqueous solution in which 500 ng of a basic fibroblast growth factor (b-FGF) (available from Kaken Pharmaceutical Co., Ltd.) in phosphate buffered saline (PBS). The sample of the silk fibroin porous material was prepared so as to contain 500 ng of the growth factor. The silk fibroin porous material impregnated with the growth factor is left still in a 12 well culture plate (available from Becton, Dickinson and Company). Then, 1 mL of Dulbecco's modified Eagle's (DME) medium (available from Gibco) was added to this silk fibroin porous material and left still in a moisture environment (condition: 37° C., 95% or more, 5% CO2). The medium was collected 96 hours later and stored at −80° C. until the measurement.

The basic fibroblast growth factor (b-FGF) was measured as described below.

Figure 30:
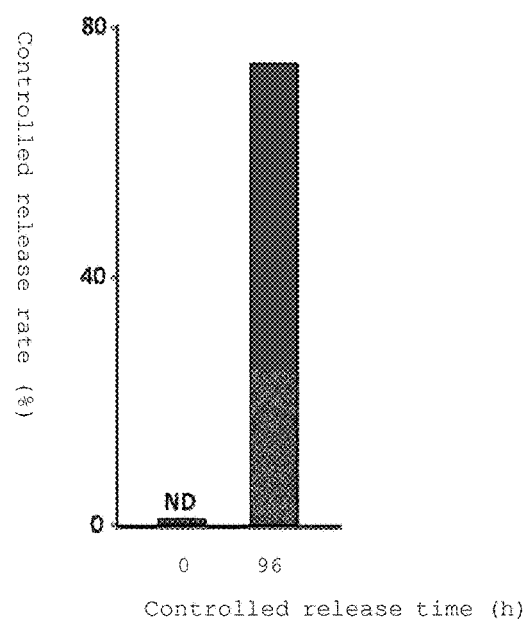
FIG. 30 shows a diagram illustrating the controlled release rate of a basic fibroblast growth factor (b-FGF) to the culture medium in Example 34.

A human b-FGF EIA kit (Research and Development, Inc.) was used. Specifically, 0.1 mL of each obtained medium was added to a 96 well microplate which immobilizes anti-b-FGF antibodies and then reacted at 37° C. for 2 hours. The wells were washed 5 times with phosphate buffered saline (PBS) containing surfactant, and then peroxidase-labelling anti-b-FGF secondary antibodies were added to the wells and then reacted at room temperature for 1 hour. Subsequently, the wells were washed 5 times in the same way, and then the color reagent was added to the wells and then reacted at room temperature for 20 minutes. Then, a reaction stopper was added, and the obtained colors were measured at 450 nm with a microplate reader. Subsequently, the controlled release amount (W3) of b-FGF was calculated from a calibration curve prepared in the same manner. The controlled release rates which were calculated from the following expression are shown in FIG. 30 as the controlled release rate of a basic fibroblast growth factor (b-FGF) to a culture medium.

(Controlled release rate of b-FGF (%))=(Controlled release amount of b-FGF in culture medium ($W3$))/500 ng×100

The controlled release amount of a basic fibroblast growth factor (b-FGF) was about 75% after 96 hours. Therefore, the silk fibroin porous material exhibits a high controlled release rate.

INDUSTRIAL APPLICABILITY

The present invention can provide a controlled drug release carrier with high a drug release rate, controlled release speed, high strength, that is easily handled, has high biocompatibility, has high water retention, and efficiently retains a drug.

The invention claimed is:

1. A controlled drug release carrier comprising:
   a silk fibroin porous material having a tensile strength between 0.1 and 400 kPa;
   a water soluble polymer within the silk fibroin porous material, the water soluble polymer comprising a polysaccharide, the polysaccharide comprising heparin or chondroitin sulfate or a combination of heparin and chondroitin sulfate; and
   a growth factor impregnated in the silk fibroin porous material.

2. The controlled drug release carrier according to claim 1, wherein the growth factor comprises at least one of a growth factor selected from the group consisting of a fibroblast growth factor (FGF), a platelet derived growth factor (PDGF), and an epidermal growth factor (EGF).

3. A controlled drug release carrier comprising:
   a silk fibroin porous material, the silk fibroin porous material having a surface and a water soluble polymer within the silk fibroin porous material, the water soluble polymer comprising a polysaccharide, the polysaccharide comprising heparin or chondroitin sulfate or a combination of heparin and chondroitin sulfate; and
   a silk fibroin film layer on the surface of the silk fibroin porous material.

4. The controlled drug release carrier according to claim 3, wherein the silk fibroin porous material has a tensile strength between 0.1 and 400 kPa.

5. The controlled drug release carrier according to claim 3, further comprising a growth factor impregnated in the silk fibroin porous material.

6. The controlled drug release carrier according to claim 5, wherein the growth factor comprises at least one of a fibroblast growth factor (FGF), a platelet derived growth factor (PDGF), and an epidermal growth factor (EGF).

* * * * *